United States Patent
Swaine

(10) Patent No.: US 7,100,818 B2
(45) Date of Patent: Sep. 5, 2006

(54) SELF-SERVICE TERMINAL

(75) Inventor: Stephen W. Swaine, Fife (GB)

(73) Assignee: NCR Corporation, Dayton, OH (US)

( * ) Notice: Subject to any disclaimer, the term of this patent is extended or adjusted under 35 U.S.C. 154(b) by 54 days.

(21) Appl. No.: 10/101,580

(22) Filed: Mar. 20, 2002

(65) Prior Publication Data

US 2002/0139842 A1 Oct. 3, 2002

(30) Foreign Application Priority Data

Mar. 28, 2001 (GB) .................. 0107689.2

(51) Int. Cl.
*G06Q 40/00* (2006.01)
*G07D 11/00* (2006.01)
*G07F 19/00* (2006.01)

(52) U.S. Cl. ..................... 235/379; 235/381

(58) Field of Classification Search ............... 235/376, 235/378–379, 382; 705/16, 10; 382/107, 382/115, 117–118, 120, 236

See application file for complete search history.

(56) References Cited

U.S. PATENT DOCUMENTS

| | | | |
|---|---|---|---|
| 5,386,103 A * | 1/1995 | DeBan et al. ............... 235/379 |
| 5,386,104 A | 1/1995 | Sime | |
| 5,568,126 A | 10/1996 | Andersen et al. | |
| 5,772,508 A | 6/1998 | Sugita et al. | |
| 5,774,591 A * | 6/1998 | Black et al. ................. 382/236 |
| 5,774,663 A | 6/1998 | Randle et al. | |
| 5,938,531 A | 8/1999 | Yasushi et al. | |
| 5,944,530 A * | 8/1999 | Ho et al. ..................... 434/236 |
| 6,002,392 A | 12/1999 | Simon et al. | |
| 6,097,927 A * | 8/2000 | LaDue ........................ 434/308 |
| 6,134,339 A * | 10/2000 | Luo ............................ 382/115 |
| 6,190,314 B1 | 2/2001 | Ark et al. | |
| 6,308,887 B1 * | 10/2001 | Korman et al. ............. 235/379 |
| 6,403,897 B1 * | 6/2002 | Bluth et al. ................. 177/144 |
| 6,457,640 B1 * | 10/2002 | Ramachandran et al. ... 235/379 |
| 6,466,232 B1 * | 10/2002 | Newell et al. .............. 345/700 |
| 6,605,038 B1 * | 8/2003 | Teller et al. ................ 600/300 |
| 6,690,351 B1 * | 2/2004 | Wong .......................... 345/156 |
| 2002/0107741 A1 * | 8/2002 | Stern et al. .................... 705/16 |

FOREIGN PATENT DOCUMENTS

EP  0 924 668 A2  6/1999

OTHER PUBLICATIONS

Rosalind. W. Picard: "Synthetic Emotion", IEEE Computers Graphics and Applications, vol. 20, No. 1, Jan. 2000 (2000-01) —Feb. 2000 (2000-02), pp. 52-53, XP002266720.

* cited by examiner

*Primary Examiner*—Thien M. Le
*Assistant Examiner*—Lisa M. Caputo
(74) *Attorney, Agent, or Firm*—Michael Chan

(57) ABSTRACT

A self service terminal (10) and method of operating a self-service terminal (10) having a user interface (14) for interacting with a user (12). The terminal (10) includes a sensing device (18, 20, or 22) for sensing physiological data associated with a user, an analyzing device (74) for analyzing the physiological data to deduce the user's emotional state, and a controlling device (72) responsive to the analyzing device (74) for adapting the terminal's interaction with the user in response to the user's emotional state.

16 Claims, 3 Drawing Sheets

WELCOME

PLEASE ENTER YOUR CARD

PLEASE ENTER
YOUR PIN

PLEASE SELECT TRANSACTION

- CASH
- TRANSFER FUNDS
- CHEQUE

- CANCEL

PLEASE ENTER AMOUNT

- £10
- £20
- £30

PLEASE REMOVE
YOUR CARD

PLEASE REMOVE
YOUR CASH

WELCOME

PLEASE ENTER YOUR CARD

PLEASE ENTER
YOUR PIN

PLEASE SELECT TRANSACTION

- CASH
- TRANSFER FUNDS
- CHEQUE

- CANCEL

PLEASE ENTER AMOUNT

- £10
- £20
- £30

AUTHORIZING TRANSACTION

HOLIDAY?

AUTHORIZING TRANSACTION

NEED A LOAN TO FUND
YOUR DREAM HOLIDAY

PLEASE REMOVE
YOUR CARD

PLEASE REMOVE
YOUR CASH

SELF-SERVICE TERMINAL

BACKGROUND OF THE INVENTION

The present invention relates to a self-service terminal (SST). In particular, the invention relates to a public access self-service terminal such as an automated teller machine (ATM) or a non-cash kiosk.

It is well known that ATMs are commonly used as a convenient source of cash and other financial transactions. Some users of ATMs desire a quick cash dispense transaction (sometimes referred to as fast cash) without viewing any promotional material (such as advertisements or marketing information) or other services (such as other transactions). Other users, however, are willing to view promotional material and/or services on ATMs depending on certain factors, such as whether they are in a hurry, whether they are interested in the type of product or service that is being promoted, or such like. If promotional material or services are presented to users at inappropriate times, or if an ATM transaction is lengthened because of presenting other services or soliciting some input from the user, then the user may be annoyed by the delay and as a result may be unsatisfied with the ATM transaction.

SUMMARY OF THE INVENTION

It is among the objects of an embodiment of the present invention to obviate or mitigate one or more of the above disadvantages or other disadvantages associated with prior art self-service terminals.

According to a first aspect of the present invention there is provided a self-service terminal having a user interface for interacting with a user, characterized in that the terminal includes sensing means for sensing physiological data associated with a user, analyzing means for analyzing the physiological data to deduce the user's emotional state, and control means responsive to the analyzing means for adapting the terminal's interaction with the user in response to the user's emotional state.

The sensing means may be implemented using a contact device, but more preferably, using a non-contact device.

Where a contact device is used, the sensing means may comprise a touch area incorporating sensors for determining the user's skin temperature, pulse rate, blood pressure, skin conductivity, and such like physiological data. A suitable touch area may be implemented by a device developed by IBM (trade mark) and called an "emotion mouse".

Where a non-contact device is used, and the terminal includes speech input, the sensing means may be implemented by a voice monitoring system for detecting changes in a user's voice. Additionally or alternatively, the sensing means may be implemented by facial recognition to detect changes in the user's facial appearance during a transaction. The sensing means may be implemented using an iris camera for imaging the user's iris and for detecting changes within the iris, such as changes to blood vessels, and such like. The sensing means may be implemented by a gesture recognition system.

The analyzing means may be implemented by any convenient algorithm for deducing a person's emotional state from physiological measurements taken from the person. An overview of such algorithms is given in chapter 6 of "Affective Computing" by Rosalind W Picard, MIT Press, 1997, ISBN 0-262-16170-2.

The control means may be implemented by a control application executing on the terminal. The control application may present a user with a sequence of screens to guide the user through a transaction. The control application may determine which screens are to be shown to the user in response to the user's emotional state as deduced by the analyzing algorithm.

The term "screen" is used herein to denote the graphics, text, controls (such as menu options), and such like, that are displayed on an SST display; the term "screen" as used herein does not refer to the hardware (for example, the LCD, CRT, or touchscreen) that displays the graphics, text, controls, and such like. Typically, when a transaction is being entered at an SST, a series of screens are presented in succession on the SST display. For example, a first screen may request a user to insert a card, a second screen may invite the user to enter his/her personal identification number (PIN), a third screen may invite the user to select a transaction, and so on.

By virtue of this aspect of the invention, the terminal is able to sense physiological data from a user during a transaction, analyze the data, and determine what to present to the user to comply with the user's emotional state. For example, the terminal may determine what transaction options to present, whether to present advertising or marketing material, if advertising is to be presented then what advertisements to present, for how long the advertisement is to last, at what point in the transaction the advertisement is to be shown, and such like.

Thus, the user's experience at the SST can be improved by personalizing a transaction to the user's emotional state. For example, if a user feels insecure then the SST may:

highlight to the user alternative SST locations at which they user may feel more secure;

display a message regarding privacy and trust to reassure the user that the transaction is secure and that the transaction provider is one that the user can trust to keep user information private;

give the user an option of more time to select a transaction option.

The SST can improve the transaction provider's marketing and advertising efficiency by targeting advertisements that are known to be more effective for a particular emotional state. For example, if the user is in a happy mood and relaxed then the user might be receptive to advertising and the SST may:

present humorous advertisements, and/or have a longer transaction sequence to provide more advertising time.

The SST may record a user's emotional experience so that future transactions conducted by that user are automatically personalized. For example, if the user is not in a relaxed mood then the user might be irritated by advertising and the SST may:

adapt the transaction to have no advertising during that transaction, or go to a customized quick transaction flow for that user the next time they use the SST.

If the SST detects particular emotional states of users, then the SST may invoke extra security measures to improve security for both the users and the SST provider. For example, if the user was detected as being under a great deal of stress then this may indicate that the user is executing a transaction under duress, or the user may be using a stolen transaction token (such as a magnetic stripe card). These extreme types of emotional states could trigger additional security measures at the SST, such as:

more security photographs being taken; and/or
security information being requested from the user.

In one embodiment the SST is an ATM.

According to a second aspect of the present invention there is provided a method of operating a self-service terminal, the method comprising the steps of: sensing physiological data associated with a user of the terminal, analyzing the physiological data to deduce the user's emotional state, and adapting the terminal's interaction with the user in response to the user's emotional state.

BRIEF DESCRIPTION OF THE DRAWINGS

These and other aspects of the present invention will be apparent from the following specific description, given by way of example, with reference to the accompanying drawings, in which.

DETAILED DESCRIPTION

Figure 1:
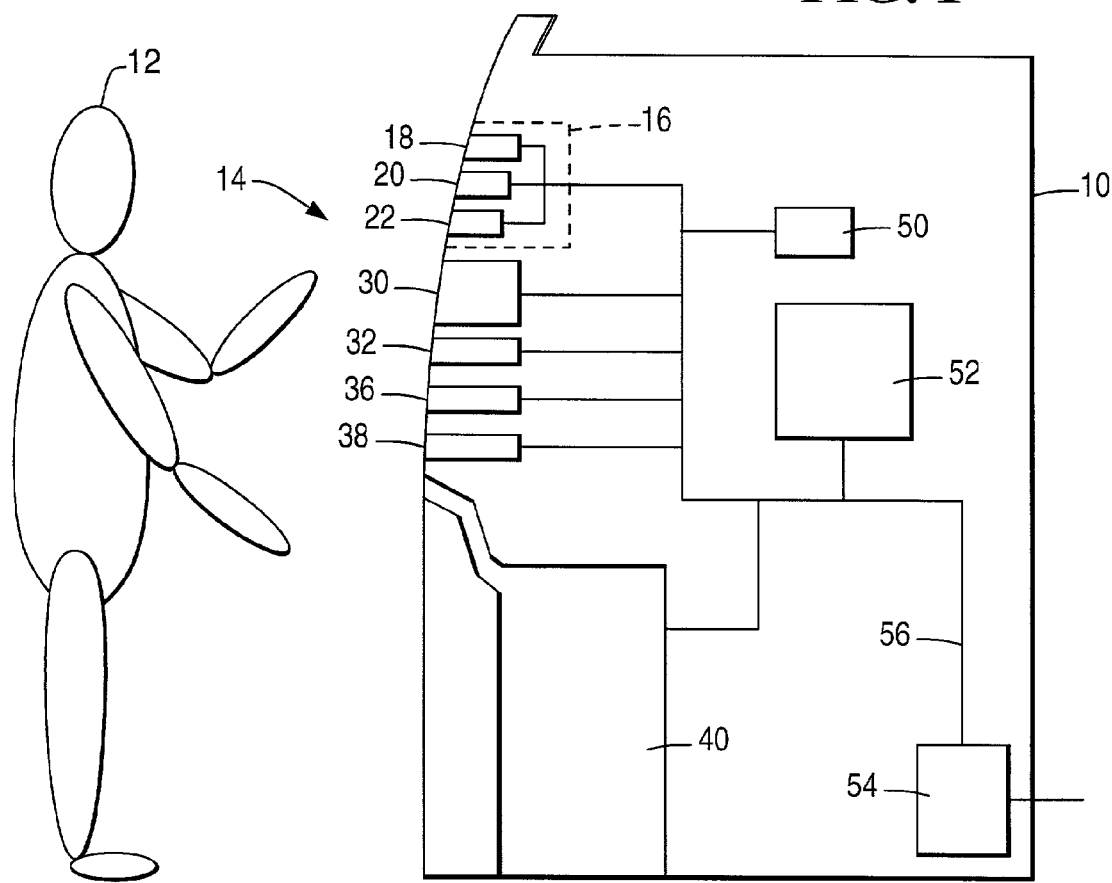
FIG. 1 is a block diagram of a self-service terminal according to one embodiment of the present invention.

Reference is now made to FIG. 1, which illustrates an SST 10 in the form of an ATM being operated by a user 12.

The ATM 10 includes a user interface 14 for outputting information to a user and for allowing a user to input information. The ATM 10 also includes sensing means 16 in the form of a camera module 18 (that includes facial recognition software), a touch plate module 20 (implemented by an "emotion mouse"), and a microphone module 22 (that includes voice recognition software).

The user interface 14 is a molded fascia incorporating: a display module 30, an encrypting keypad module 32, and a plurality of slots aligned with modules located behind the fascia. The slots include a card entry/exit slot (not shown) that aligns with a magnetic card reader/writer (MCRW) module 36, a printer slot (not shown) that aligns with a printer module 38, and a cash dispense slot (not shown) that aligns with a cash dispense module 40.

The ATM 10 also includes an internal journal printer module 50 for creating a record of all transactions executed by the ATM 10, an ATM controller module 52 for controlling the operation of the various modules (18 to 50), and a network connection module 54 for communicating with a remote transaction host (not shown) for authorizing transactions. All of the modules (18 to 54) within the ATM 12 are interconnected by an internal bus 56 for securely conveying data.

Figure 2:
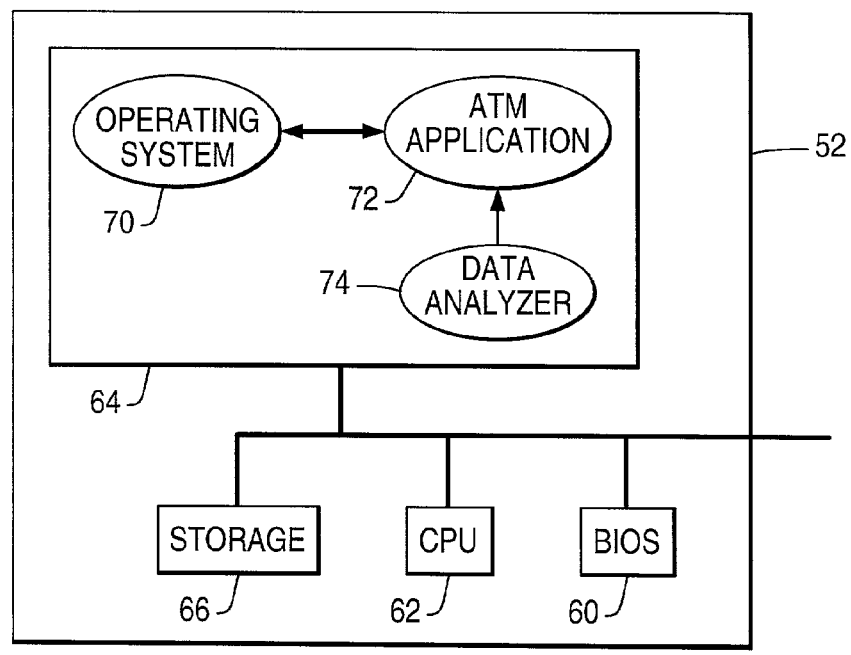
FIG. 2 is a block diagram of a part (the controller) of the terminal of FIG. 1.
Figure 3A:
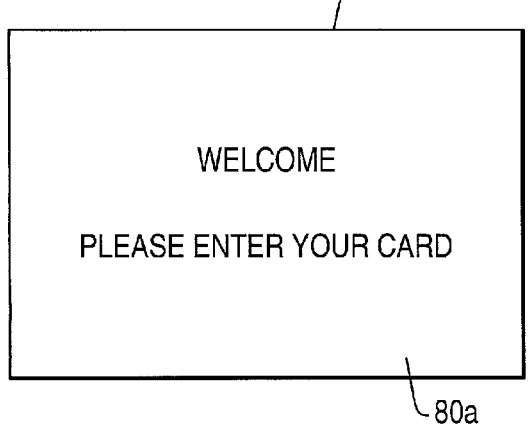
FIGS. 3A to 3F illustrate a sequence of screens presented to one user of the terminal of FIG. 1.
Figure 3B:
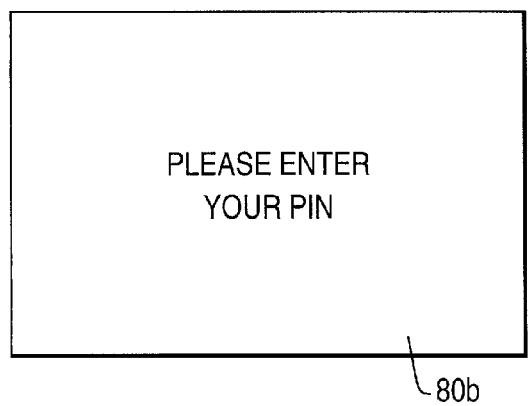
Figure 3C:
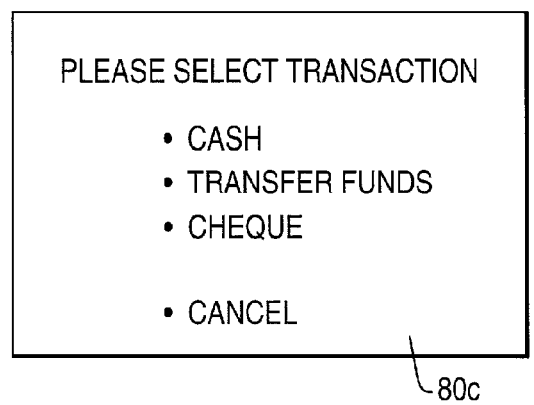
Figure 3D:
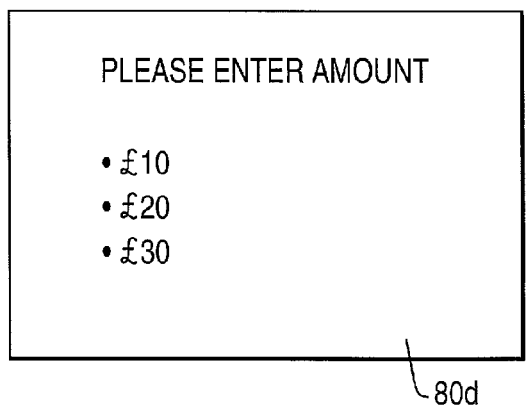
Figure 3E:
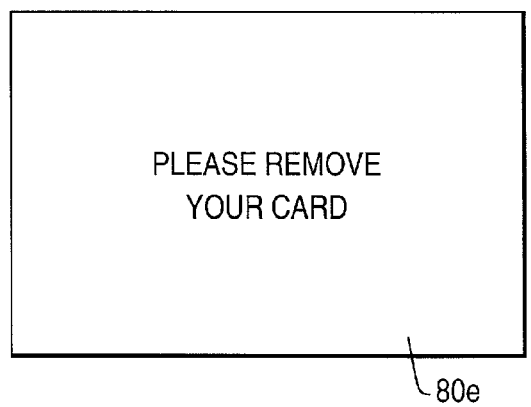
Figure 3F:
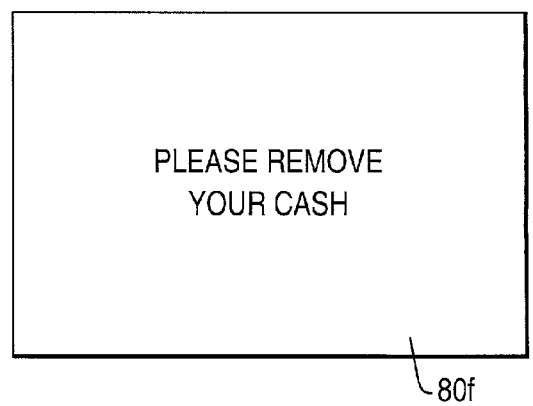
Figure 4A:
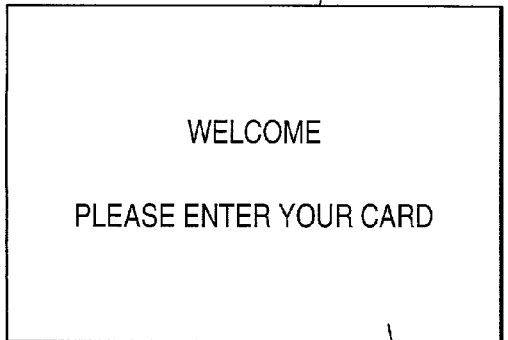
FIGS. 4A to 4H illustrate a sequence of screens presented to another user of the terminal of FIG. 1.
Figure 4B:
Figure 4C:
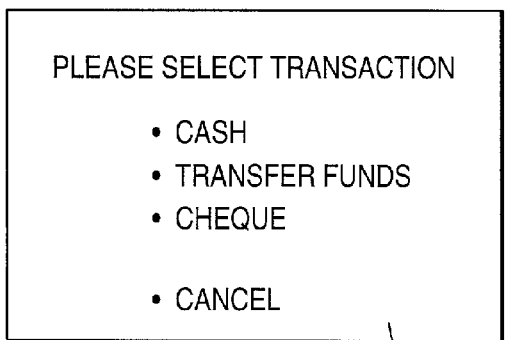
Figure 4D:
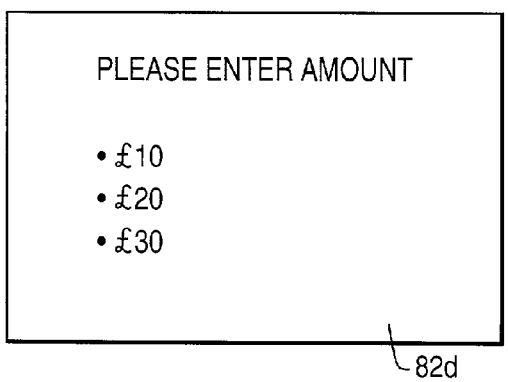
Figure 4E:
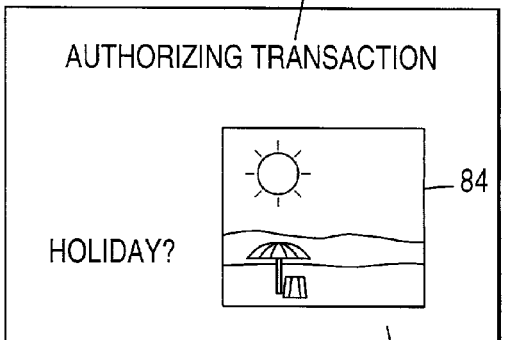
Figure 4F:
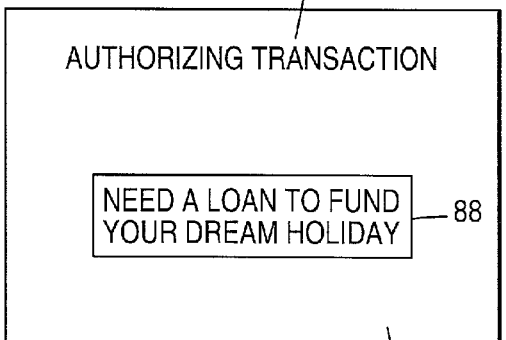
Figure 4G:
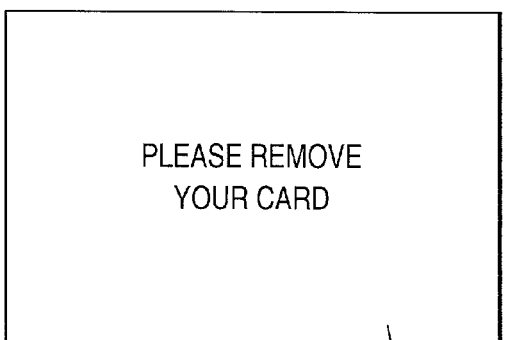
Figure 4H:
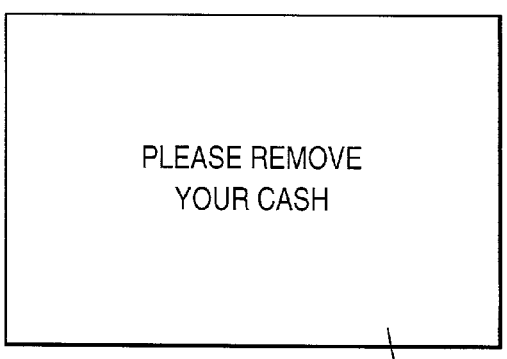

The ATM controller module 52 is shown in more detail in FIG. 2. The controller 52 comprises a BIOS 60 stored in non-volatile memory, a microprocessor 62, associated main memory 64, and storage space 66 in the form of a magnetic disk drive.

In use, the ATM 12 loads an operating system kernel 70, an ATM application program 72, and a data analyzing program 74 into the main memory 64.

The ATM application program 72 is used to control the operation of the ATM 12. In particular, the ATM application program 72: provides the sequence of screens used in each transaction (referred to as the application flow); monitors the condition of each module within the ATM (state of health monitoring); and interfaces with the analyzing program 74.

The analyzing program 74 implements a discriminant function analysis model for analyzing data received from the sensor modules 18 to 22; however, any other convenient analyzing program may be used. The analyzing program 74 processes data received from one or more of the sensor modules (camera 18, touch plate 20, or microphone 22) to deduce the emotional state of the user 12.

The analyzing program 74 selects an emotion category that is the closest match to the user's emotional state, and outputs a code representing this category to the ATM application program 72. In this embodiment, the categories are: anger, hurriedness, fear, happiness, sadness, and surprise.

The ATM application program 72 receives this code and adapts the transaction flow according to the emotional state represented by this code. This is implemented by the ATM application program 72 accessing a stored look-up table (not shown) having an index entry for each code. Each code in the look-up table has a unique transaction flow associated with it.

An example of a typical transaction at the ATM 10 will now be described with reference to FIGS. 3A to 3F, which illustrate the sequence of screens presented to the user 12.

When the user 12 approaches the ATM 10 he is presented with a welcome screen 80a (FIG. 3A) on display 30 inviting him to insert his card. After inserting his card, the user 12 is presented with a screen 80b (FIG. 3B) inviting him to enter his PIN, and the ATM application program 72 activates the sensors 18 to 22 to capture physiological data about the user 12.

The ATM application receives data from the sensors 18 to 22 and conveys this data to the data analyzing program 74. Data analyzing program 74 processes the received data, deduces the user's emotional state from the data, generates a category code representing the user's emotional state, and conveys this code to the ATM application program 72. The ATM application program 72 accesses the look-up table (not shown) using the category code received from the data analyzing program 74 to determine what sequence of screens should be presented to the user 12. In this example, the user's state is hurriedness, so the sequence of screens is that for the shortest possible transaction time.

The ATM application program 72 then presents the user 12 with a screen 80c (FIG. 3C) listing transaction options available. After the user 12 has selected the withdraw cash option, the ATM application 72 presents the user with a screen 80d (FIG. 3D) indicating cash amounts available. Once the user has selected a cash amount, the ATM application authorizes the transaction, presents a screen 80e (FIG. 3E) inviting the user to remove his card, then a screen 80f (FIG. 3F) inviting the user to remove the requested cash.

An example of a typical transaction at the ATM 10 will now be described with reference to FIGS. 4A to 4H, which illustrate the sequence of screens presented to another user (or the same user as for FIGS. 3A to 3F but in a different emotional state).

When the user approaches the ATM 10 he is presented with a welcome screen 82a (FIG. 4A) on display 30 inviting him to insert his card. After inserting his card, the user is presented with a screen 82b (FIG. 4B) inviting him to enter his PIN, and the ATM application program 72 activates the sensors 18 to 22 to capture physiological data about the user.

As in the previous example, the ATM application 72 receives data from the sensors 18 to 22 and conveys this data to the data analyzing program 74. Data analyzing program 74 processes the received data, deduces the user's emotional state from the data, generates a category code representing the user's emotional state, and conveys this code to the ATM application program 72. The ATM application program 72 accesses its look-up table (not shown) using the category code received from the data analyzing program 74 to determine what sequence of screens should be presented to the user. In this example, the user's state is happiness, so the sequence of screens includes an advertisement for a holiday, and promotional material for a loan.

The ATM application program 72 then presents the user with a screen 82c (FIG. 4C) listing transaction options available. After the user has selected the withdraw cash option, the ATM application 72 presents the user with a screen 82d (FIG. 4D) indicating cash amounts available.

Once the user has selected a cash amount, the ATM application 72 authorizes the transaction, and presents the user with a screen 82e (FIG. 4E) incorporating a video 84 (in MPEG format) advertising a holiday, the screen 82e also includes text 86 informing the user that the requested transaction is being authorized.

Once the video (which lasts approximately four seconds) has finished, the ATM application 72 then presents the user with a screen 82f (FIG. 4F) incorporating promotional material 88 for a loan.

The ATM application 72 then presents a screen 82g (FIG. 4G) inviting the user to remove his card, and once the card has been removed, a screen 82h (FIG. 4H) inviting the user to remove the requested cash.

It will be appreciated that this embodiment has the advantage that a user is presented with a transaction sequence that is most likely to fulfil the user's expectations by matching a transaction to the user's emotional state.

Various modifications may be made to the above described embodiment within the scope of the invention, for example, in other embodiments, the user may be asked to touch the touch plate 20 at the beginning of the transaction so that the touch plate can collect physiological data from the user's hand. In other embodiments, multiple algorithms may be used to implement the analyzing program 74, one for each sensor module 18 to 22. In other embodiments, different sensors may be used. In other embodiments, the touch plate sensor may be implemented on the keys of the encrypting keypad so that physiological measurements can be taken while the user is entering his PIN or other transaction details. In other embodiments, the user's emotional state may be continually monitored during the transaction flow so that the transaction flow may be changed at any point in response to the user's emotional state; for example, an advertisement may be stopped if a user's emotional state changes from being happy or relaxed to being unhappy or angry. In other embodiments, different emotional states may be categorized than those described in the above embodiment.

What is claimed is:

1. An automated teller machine (ATM) for providing an ATM customer with a tailored cash dispense transaction based upon the ATM customer's emotional state, the ATM comprising:
    a cash dispenser for dispensing cash to the ATM customer to fulfill the cash dispense transaction;
    a display for presenting a series of display screens to the ATM customer to guide the ATM customer through the cash dispense transaction;
    at least one sensor which senses physiological data associated with the ATM customer;
    an analyzer which analyzes the physiological data from the at least one sensor to provide either a first category code which is indicative of the ATM customer being in a first emotional state or a second category code which is indicative of the ATM customer being in a second emotional state which is different from the first emotional state; and
    a controller for (i) tailoring the series of display screens to include a first set of display screens when the analyzer provides the first category code which is indicative of the ATM customer being in the first emotional state, (ii) tailoring the series of display screens to include promotional material not included in the first set of display screens when the analyzer provides the second category code which is indicative of the ATM customer being in the second emotional state, so that the ATM customer is not presented with the promotional material when the ATM customer is in the first emotional state and is presented with the promotional material when the ATM customer is in the second emotional state, and (iii) instructing the cash dispenser to dispense cash to the ATM customer during the cash dispense transaction.

2. An ATM according to claim 1, wherein the at least one sensor includes a contact device.

3. An ATM according to claim 1, wherein the at least one sensor includes a number of touch-sensitive sensors for determining a number of types of physiological data associated with an ATM customer.

4. An ATM according to claim 3, wherein types of physiological data include skin temperature, pulse rate, blood pressure, and skin conductivity.

5. An ATM according to claim 1, wherein the at least one sensor includes a non-contact device.

6. An ATM according to claim 1, wherein the at least one sensor includes a voice monitoring system for detecting changes in an ATM customer's voice.

7. An ATM according to claim 1, wherein the at least one sensor includes a facial recognition system for detecting changes in an ATM customer's facial appearance during an ATM transaction.

8. An ATM according to claim 1, wherein the at least one sensor includes a human iris camera for imaging an ATM customer's iris and for detecting changes within the iris.

9. An ATM according to claim 1, wherein the at least one sensor includes a gesture recognition system.

10. An ATM according to claim 1, wherein the analyzer includes an algorithm for deducing an ATM customer's emotional state based upon sensed physiological data associated with the ATM customer.

11. An ATM according to claim 1, wherein the controller includes a control application executing on the ATM.

12. A method of operating an automated teller machine (ATM) based upon an ATM customer's emotional state to fulfill a cash dispense transaction, the method comprising the steps of:
    sensing physiological data associated with the ATM customer;
    analyzing the physiological data to provide either a first category code which is indicative of the ATM customer being in a first emotional state or a second category code which is indicative of the ATM customer being in a second emotional state which is different from the first emotional state;
    tailoring a series of display screens presented to the ATM customer to include a first set of display screens when the first category code which is indicative of the ATM customer being in the first emotional state is provided;
    tailoring the series of display screens to include promotional material not included in the first set of display screens when the second category code which is indicative of the ATM customer being in the second emotional state is provided, so that the ATM customer is not presented with the promotional material when the ATM customer is in the first emotional state and is presented with the promotional material when the ATM customer is in the second emotional state; and dispensing cash to the ATM customer to fulfill the cash dispense transaction.

13. A method according to claim 12, wherein the step of sensing physiological data includes the step of sensing at least one of skin temperature, pulse rate, blood pressure, and skin conductivity.

14. A method according to claim 12, wherein the step of sensing physiological data includes the step of detecting changes in an ATM customer's voice.

15. A method according to claim 12, wherein the step of sensing physiological data includes the step of detecting changes in an ATM customer's facial appearance during a transaction carried out at the ATM.

16. A method according to claim 12, wherein the step of sensing physiological data includes the steps of imaging an ATM customer's iris and detecting changes within the iris.

* * * * *